United States Patent [19]
Fukaya et al.

[11] Patent Number: 5,573,650
[45] Date of Patent: Nov. 12, 1996

[54] GAS SENSOR

[75] Inventors: Kenji Fukaya, Chiryu; Masatoshi Suzuki, Nagoya; Masahiro Hamaya, Anjo; Makoto Hori, Ogaki, all of Japan

[73] Assignee: Nippondenso Co., Ltd., Kariya, Japan

[21] Appl. No.: 186,586

[22] Filed: Jan. 26, 1994

[30] Foreign Application Priority Data

Jan. 28, 1993 [JP] Japan ................................. 5-034718
May 27, 1993 [JP] Japan ................................. 5-148562

[51] Int. Cl.⁶ ................................................. G01N 27/407
[52] U.S. Cl. ........................ 204/424; 204/400; 204/426; 204/427; 204/428
[58] Field of Search ........................... 204/421–429

[56] References Cited

U.S. PATENT DOCUMENTS 4,310,401  1/1982  Stahl ................................. 204/426
4,556,475  12/1985 Bayha et al. ....................... 204/427
5,246,562  9/1993  Weyl et al. ......................... 204/424

Primary Examiner—T. Tung
Attorney, Agent, or Firm—Cushman, Darby, & Cushman, L.L.P.

[57] ABSTRACT

A gas sensor includes a sensor element having one end portion exposed to gas to be measured. A plurality of electrodes are provided on the other end portion of the sensor element. A plurality of terminal contacts are resiliently held in electrical contact with the electrodes, respectively, in such a manner that the terminal contacts hold the other end portion of the sensor element therebetween. The electrodes are so provided on the sensor element that the terminal contacts abut against the electrodes to prevent the sensor element from being moved axially and laterally.

12 Claims, 11 Drawing Sheets

GAS SENSOR

FIELD OF THE INVENTION AND RELATED ART STATEMENT

The present invention relates to a gas sensor, for example, for detecting an oxygen concentration in exhaust gas from an engine.

An oxygen sensor used for achieving an optimum combustion control comprises a sensor element of ceramics which is formed into an elongate plate, and is housed in a tubular housing to be mounted on an exhaust pipe, and a distal end portion of the sensor element is exposed to exhaust gas. In order to take out a signal from the sensor element easily and inexpensively, take-out electrodes are mounted on a proximal end portion of the sensor element, and contact terminals, connected respectively to one ends of lead wires extending from the exterior of the housing, are resiliently contacted with these electrodes, respectively, as disclosed, for example, in U.S. Pat. No. 4,556,475.

In this construction, since the pressures of the contact terminals against the electrodes act only in a direction of holding of the sensor element between the contact terminals, the sensor element is movable in a direction perpendicular to the direction of these holding forces. Therefore, the sensor element is sometimes displaced out of position by vibrations or the like, so that electrical connection with the contact terminals is interrupted, and in the worst case the contact terminal is brought into contact with other take-out electrode than its mating electrode.

OBJECT AND SUMMARY OF THE INVENTION

It is an object of the present invention to provide a gas sensor in which an adequate interval between take-out electrodes is secured, and which is prevented from being displaced, thereby enhancing reliability in taking-out of a signal.

To this end, according to the present invention, there is provided a gas sensor comprising: a sensor element which is to be exposed at one end portion thereof to gas to be measured; a tubular housing holding said sensor element; a plurality of electrode portions provided on the other end portion of said sensor element; a plurality of terminal contacts resiliently held in electrical contact with said plurality of electrode portions, respectively, said terminal contacts holding the other end portion of said sensor element therebetween; and means provided at portions of contact between said electrode portions and said contact terminals for preventing said sensor element from moving laterally in a direction intersecting a direction of contact pressures applied by said terminal contacts.

DETAILED DESCRIPTION OF THE PREFERRED EMBODIMENTS

Figure 1:
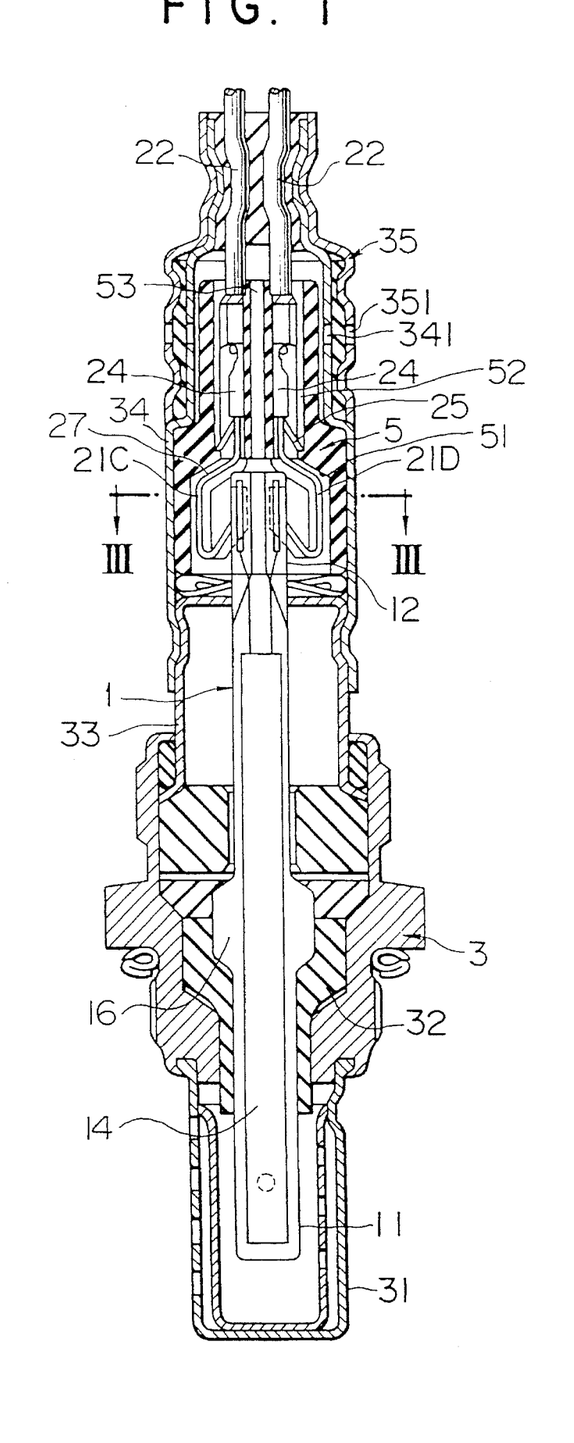
FIG. 1 is a longitudinal cross-sectional view of one preferred embodiment of a gas sensor of the present invention.
Figure 2:
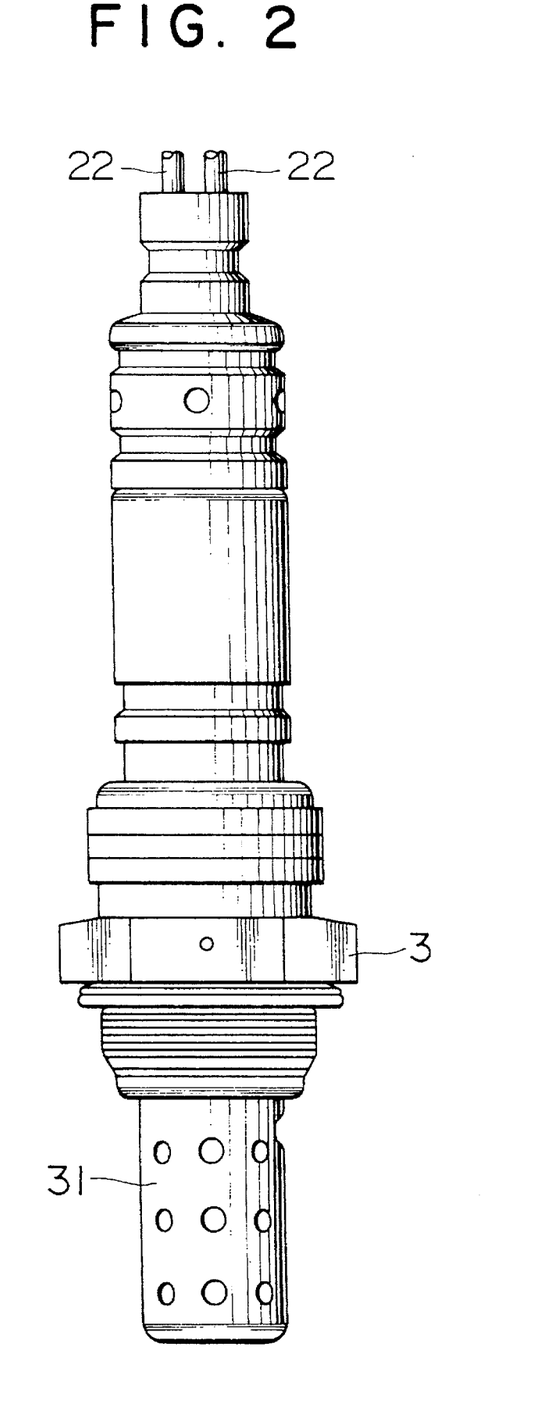
FIG. 2 is a side-elevational view of the gas sensor of FIG. 1.

Referring to FIG. 1, an element cover 31 of a double-tube construction with a closed bottom, which has a number of through holes, is mounted on a lower end of a metal tubular housing 3. The housing 3 is adapted to be fixedly screw-mounted to a wall of an exhaust pipe. A one end portion (distal end portion) 11 of a sensor element 1 in the form of an elongate plate is disposed within the element cover 31.

The other end portion (proximal end portion) 12 of the sensor element 1 extends through an insulator 32 mounted on an inner periphery of the housing 3 and a body cover 33 caulked to an end opening of the housing 3 into a dust cover 34 mounted on the body cover 33.

An air introduction hole 351 is formed through a filter cover 35 covering the outer periphery of a portion of the dust cover 34, and a vent hole 341 is formed through the dust cover 34. The atmosphere is introduced into an air introduction passage 15 of the sensor element 1 through the air introduction hole 351, the vent hole 341 and a central through hole 53 of the insulator 5.

Figure 3:
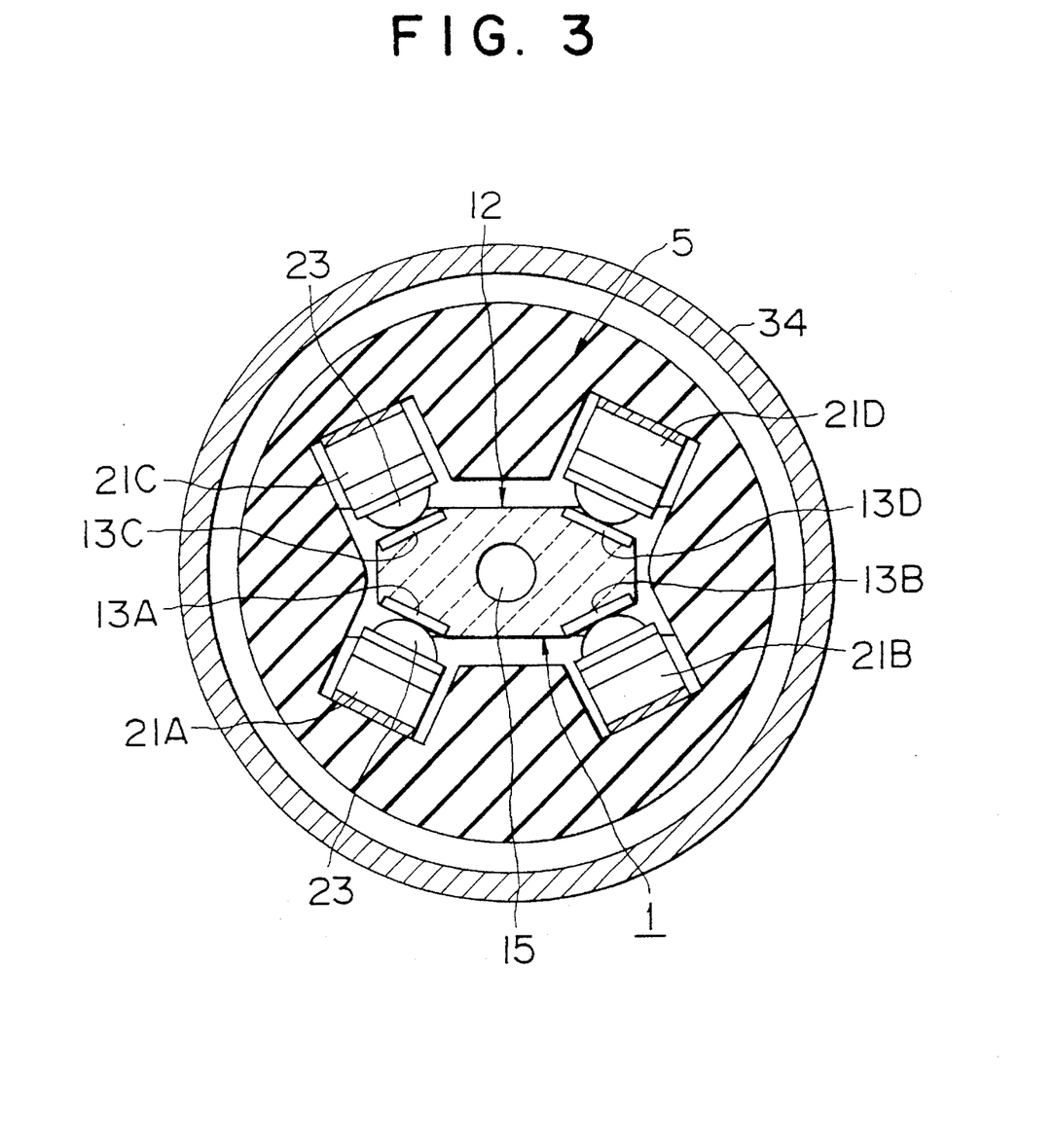
FIG. 3 is a cross-sectional view of the gas sensor taken along the line III—III of FIG. 1.
Figure 4:
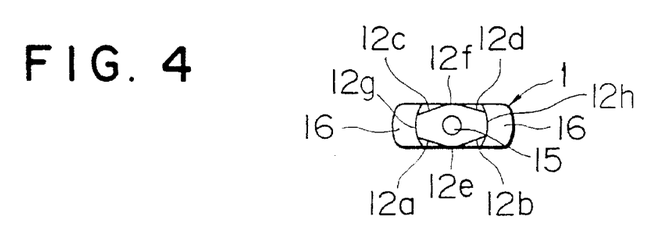
FIG. 4 is a plan view of a sensor element.
Figure 5:
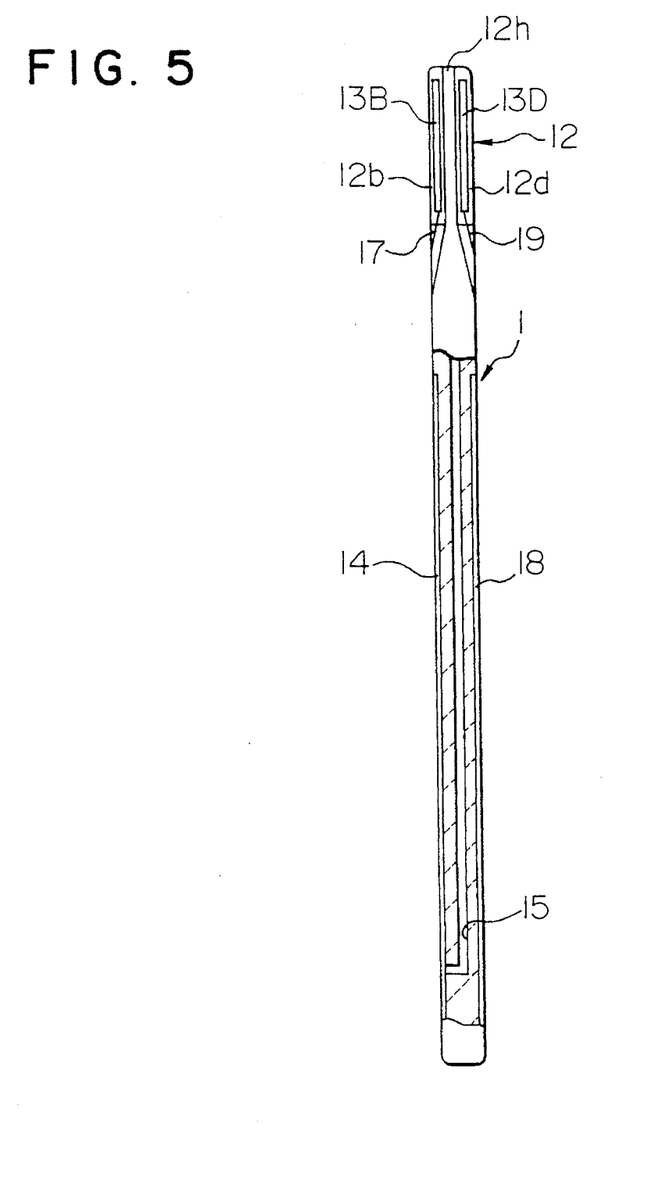
FIG. 5 is a side-elevational view of the sensor element.

As shown in detail in FIGS. 3, 4 and 5, a body of the sensor element 1 comprises an elongate plate of alumina or ceramics having a rectangular cross-section and a pair of projections 16 for positioning the sensor element 1 in an axial direction formed respectively on opposite side surfaces of the sensor element 1 at an axial intermediate position thereof. An elongate, thin plate 14 of zirconia serving as a sensor portion is bonded to a front face of the sensor element 1. The air introduction passage 15 is formed in the sensor element 1 and opened to the back side of the thin plate 14 at the distal end portion 11 of the sensor element 1. With this arrangement, according to a known principle, an output, produced in accordance with a difference in oxygen concentration between introduced air and exhaust gas, is obtained at the sensor portion, and this output is fed via lead electrodes 17 to take-out electrodes 13A and 13B (later described in detail) formed on the proximal end portion 12 of the sensor element 1.

A thin plate 18 of a ceramics material is bonded to a face opposite to the front face of the sensor element 1 so as to serve as a heater portion. Lead electrodes 19 (only one is shown) extending from this heater portion are also connected to take-out electrodes 13C and 13D (later described in detail) formed on the proximal end portion 12 of the sensor element 1.

Figure 6:
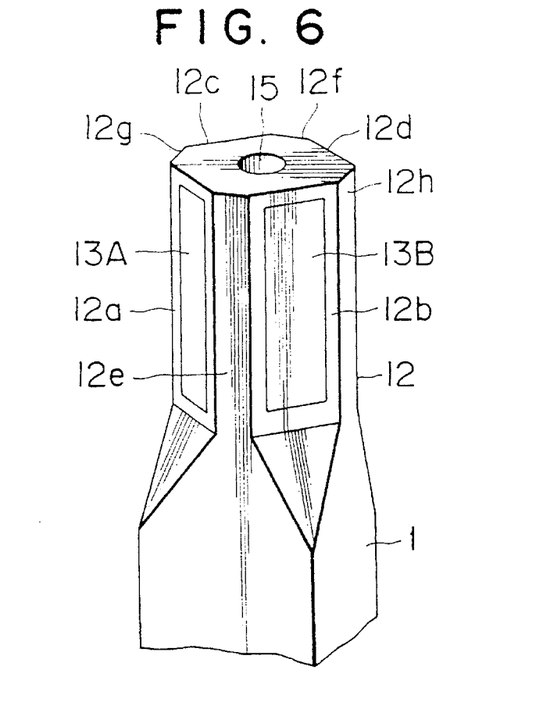
FIG. 6 is an enlarged, perspective view of a proximal end portion of the sensor element.

As shown in detail in FIG. 6, four corners of the proximal end portion 12 of the sensor element 1 are chamfered, so that the proximal end portion 12 is of an octagonal cross-section having four slanting surfaces 2a, 12b, 12c and 12d and four side surfaces 12e, 12f, 12g and 12h. The take-out electrodes 13A and 13B for the sensor portion are formed on the slanting surfaces 12a and 12b, respectively, and the take-out electrodes 13C and 13D for the heater portion are formed on the slanting surfaces 12c and 12d, respectively.

Figure 7:
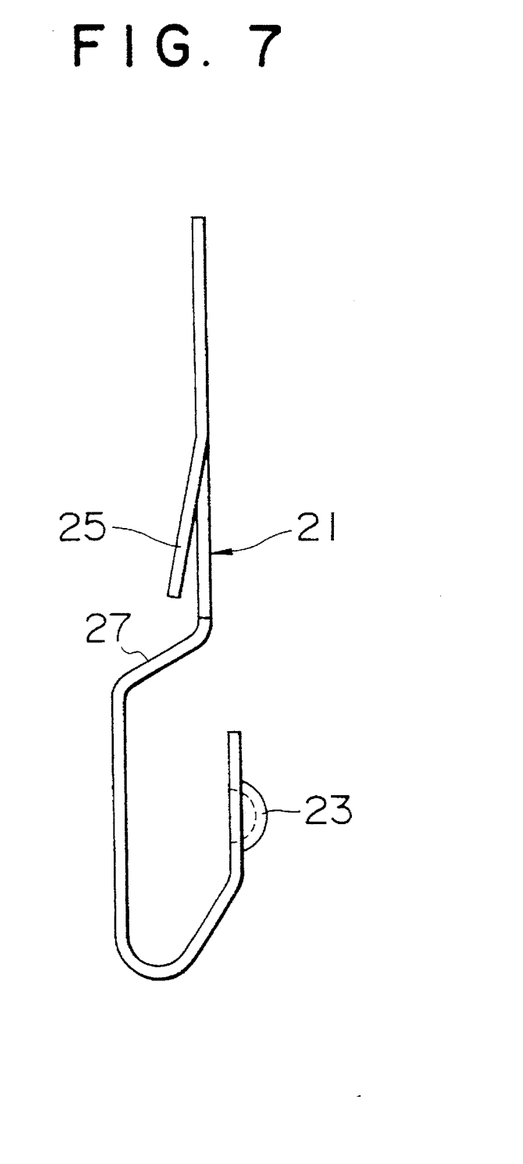
FIG. 7 is a side-elevational view of a contact terminal.
Figure 8:
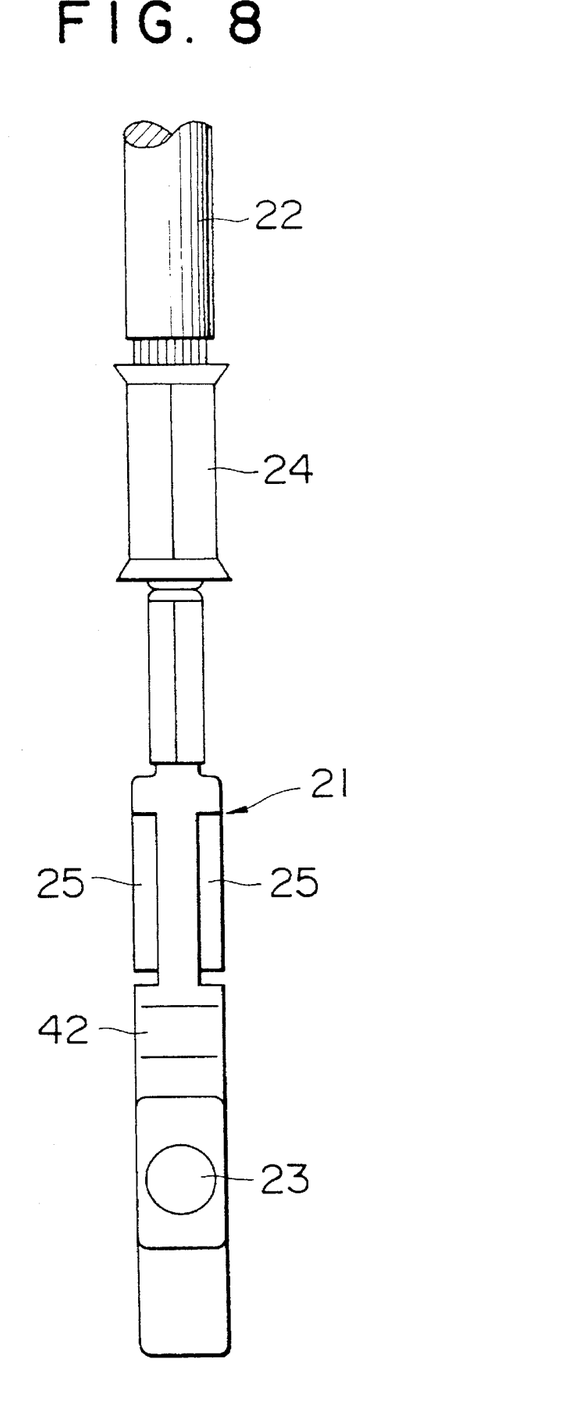
FIG. 8 is a front-elevational view of the contact terminal.

Contact terminals 21A, 21B, 21C and 21D each made of a spring material are held in electrical contact with the take-out electrodes 13A to 13D, respectively. Each of the contact terminals 21A to 21D is formed by bending an elongate spring material plate into a generally U-shape (FIGS. 7 and 8). These contact terminals 21A to 21D are housed in position within a tubular ceramic insulator 5 disposed within the dust cover 34. Contact points 23 (FIG. 3) at one ends of these contact terminals 21A to 21D are resiliently contacted with the take-out electrodes 13A to 13D, respectively. Lead wires 22 (FIG. 1) extending from the exterior of the oxygen sensor are connected at their one ends respectively to the other ends of the contact terminals 21A to 21D by respective caulking connectors 24.

With this construction, the front and rear faces (lower and upper faces in FIG. 9) of the proximal end portion 12 of the sensor element 1 have sufficiently wide areas, which faces are constituted by the slanting surfaces 12a, 12b and the side surface 12e, and the slanting surfaces 12c, 12d and the side surface 12f, respectively. Therefore the take-out electrodes 13A and 13B formed respectively on the slanting surfaces 12a and 12b are apart from each other by a large distance. The take-out electrodes 13C and 13D formed respectively on the slanting surfaces 12c and 12d are also apart from each other by a large distance. Further a contact pressure F applied from a contact terminal to a take-out electrode is directed perpendicularly to a slanting surface toward an axis of the sensor element 1. One component of the contact pressure F serves to hold the sensor element 1 between opposite contact terminals. The resultant force of the other components of the contact pressures F prevents the sensor element 1 from being moved laterally from its original position (that is, in a direction perpendicular to the sensor element holding force).

Figure 10:
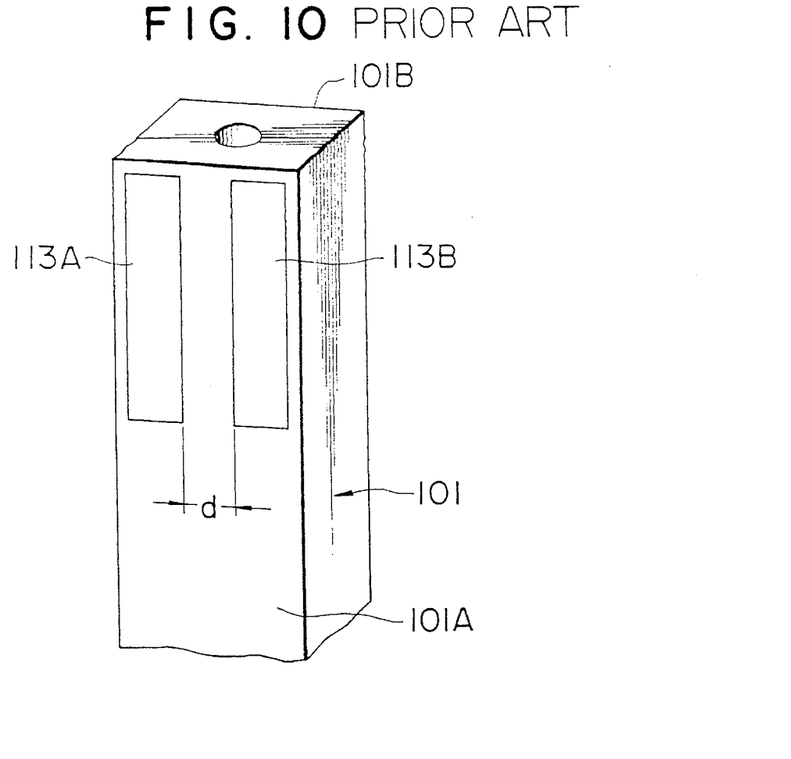
FIG. 10 is a perspective view of a proximal end portion of a conventional sensor element.
Figure 11:
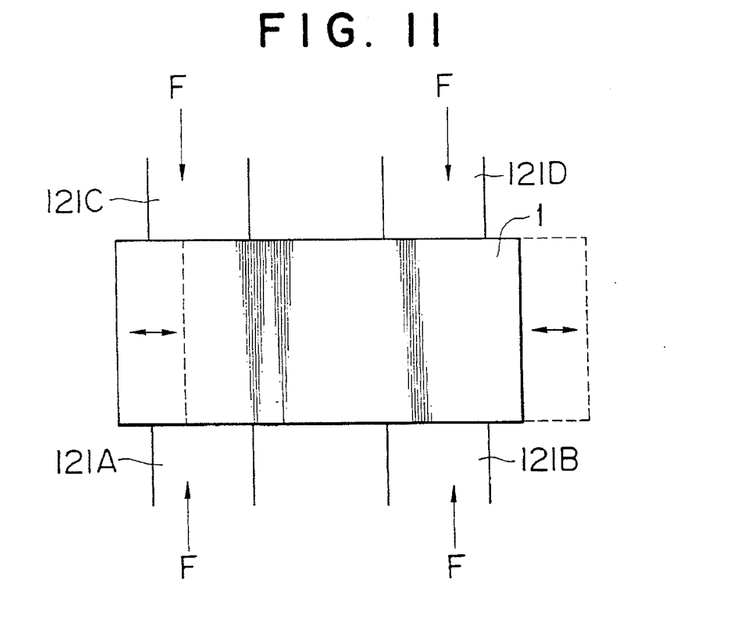
FIG. 11 is a schematic plan view of the proximal end portion of the sensor element of FIG. 10.

On the other hand, in a conventional construction shown in FIG. 10, a pair of electrodes 113A and 113B and another pair of electrodes (not shown) are formed respectively on opposite faces 101A and 101B of a sensor element 101 having a rectangular transverse cross-section. In this case, as shown in FIG. 11, contact pressures F applied respectively from contact terminals 121A to 121D act only in a direction of holding of the sensor element 101 between the opposed contact terminals, and therefore the sensor element 101 may move in directions perpendicular to the sensor element holding direction (that is, in a lateral direction and in an axial direction perpendicular to the sheet of FIG. 11).

Figure 9:
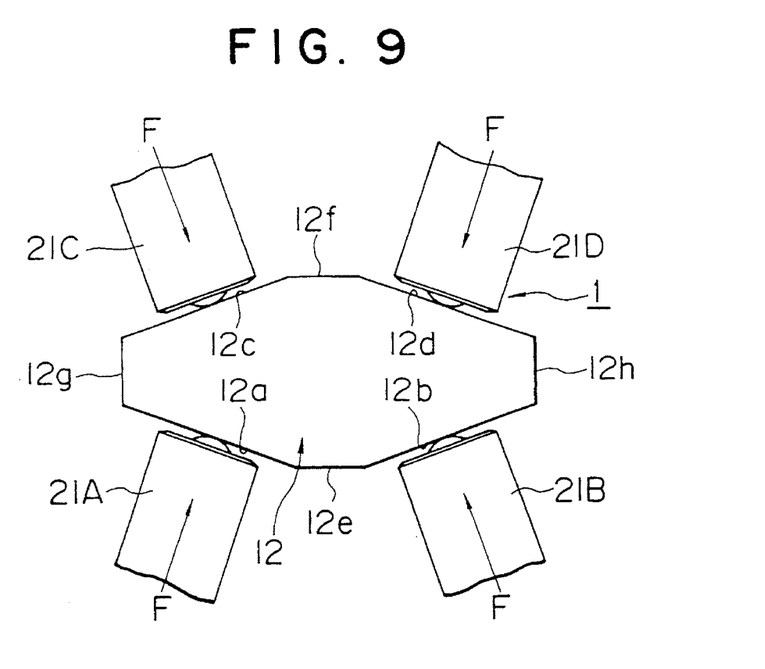
FIG. 9 is a schematic plan view of a proximal end portion of the sensor element of FIG. 6.

In the present invention, without the provision of any particular positioning means, the sensor element 1 can be positively positioned by the contact pressures of the contact terminals 21A to 21D, and the interval between the parallel contact electrodes 13A and 13B, as well as the interval between the parallel contact electrodes 13C and 13D, is sufficiently large. Therefore, with this simple and inexpensive construction, the electrical connection of each of the contact terminals to its mating take-out electrode can be positively ensured without causing any wrong contact.

Figure 12:
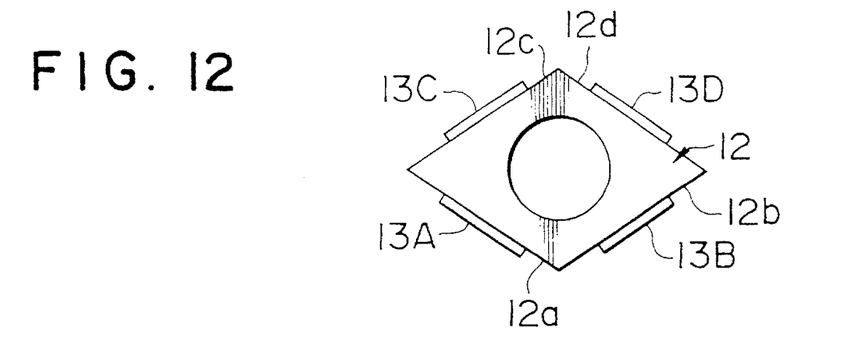
FIGS. 12–14 are schematic plan views of the respective proximal end portions of modified sensor elements of the present invention.

FIG. 12 shows a modified sensor element in which its proximal end portion 12 is of a generally quadrilateral cross-section having only four slanting surfaces 12a, 12b, 12c and 12d, and take-out electrodes 13A, 13B, 13C and 13D are formed on the slanting surfaces 12a to 12d, respectively. With this construction, similar effects as obtained with the above embodiment can be achieved.

Figure 13:
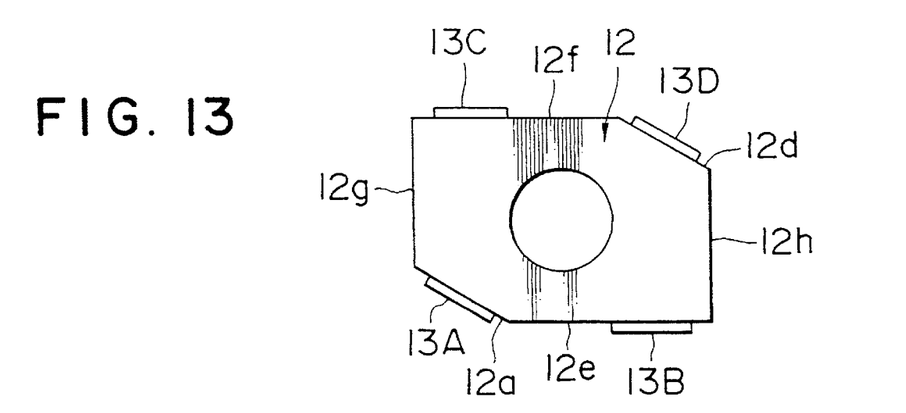

FIG. 13 shows another modified sensor element in which its proximal end portion 12 has two slanting surfaces 12a and 12d, disposed symmetrically with respect to an axis of the sensor element, and take-out electrodes 13A, 13B, 13C and 13D are formed on the slanting surfaces 12a and 12d, and side surface 12e and 12f, respectively. With this construction, similar effects can be achieved.

Figure 14:
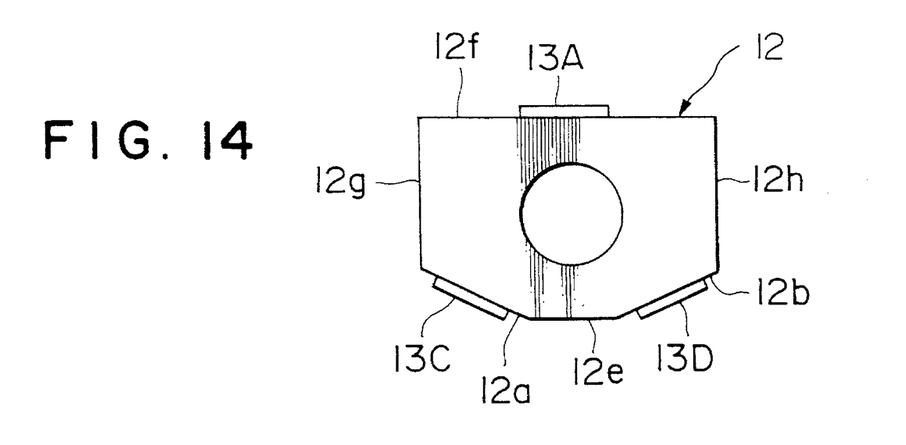

In case that one of sensor signal lines is grounded, and then only three take-out electrodes 13A, 13C and 13D are needed, the sensor element shown in FIG. 14 may be applicable. In such sensor element, two corners of one face 12e of the proximal end portion of the sensor element are chamfered to provide slanting surfaces 12a and 12b. The take-out electrodes 13C and 13D are formed on these slanting surfaces 12a and 12b, respectively, and the take-out electrode 13A is formed on the other face 12f of the proximal end portion of the sensor element. With this construction, similar effects can be achieved.

In the embodiment shown in FIG. 1, the displacement of the sensor element 1 in the axial direction can also be prevented. As shown in FIGS. 7 and 8, the contact terminal 21 comprises an elongate spring material plate which is bent into a generally U-shaped to provide a bent portion 27 and the contact projection 23 of a semi-spherical shape formed on the end portion of the contact terminal. Opposite edge portions of a central portion of the contact terminal 21 are stamped and raised to provide a pair of retaining pieces 25 extending obliquely. One end of the lead wire 22 is connected to the proximal end of the contact terminal 21 by the caulking connector 24.

The contact terminals 21A to 21D are housed within the tubular ceramic insulator 5 received within the dust cover 34 (FIG. 1), and the contact points 23 of these contact terminals 21A to 21D are respectively in contact with the take-out electrodes 13A to 13D of the sensor element 1 (FIG. 3). The insulator 5 has a first half (upper portion) of a smaller diameter and a second half (lower portion) of a larger diameter. Those portions of an inner surface of the second half of the insulator 5 which face the take-out electrodes 13A to 13D, respectively, are recessed radially outwardly into a rectangular shape. Each of the bent portions 27 of the contact terminals 21A to 21D is received in the respective recesses close to a step portion 51 which is formed on the inner surface of the insulator 5.

Figure 15:
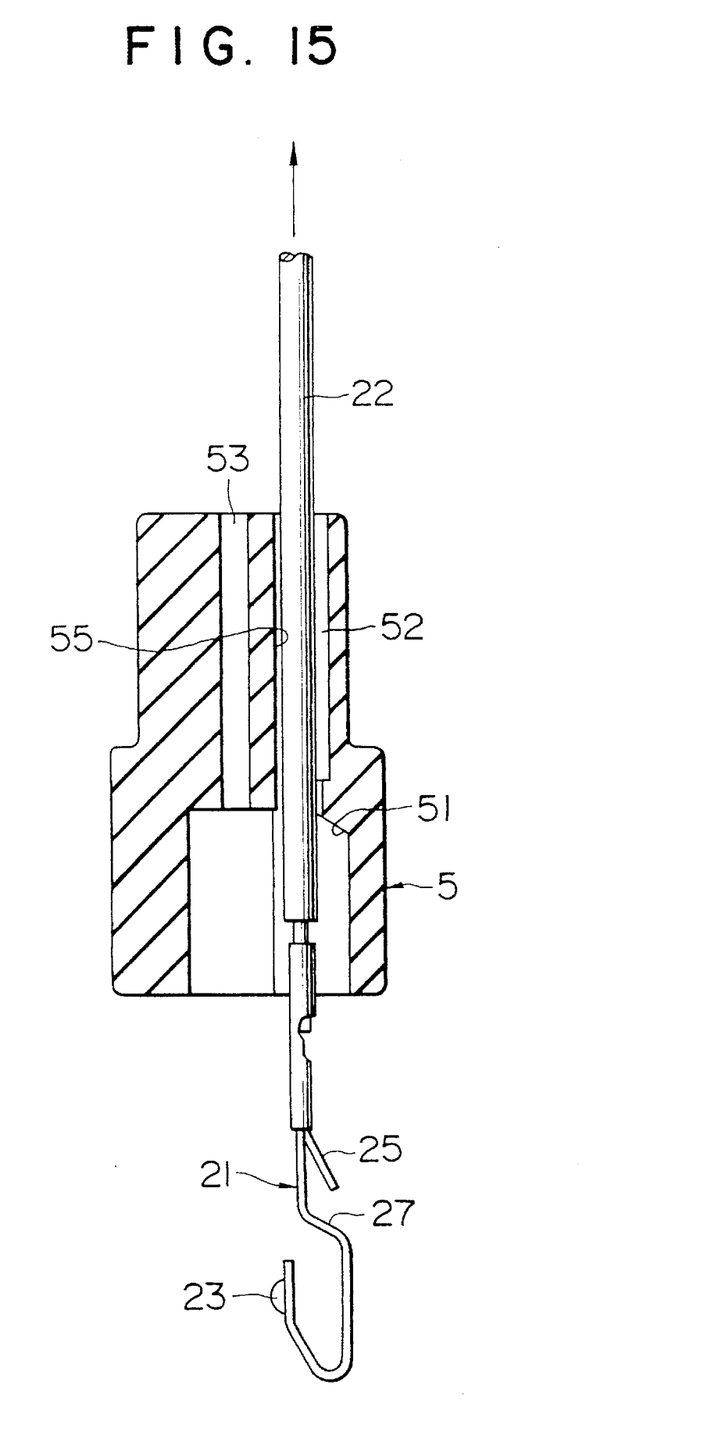
FIG. 15 is a cross-sectional view showing an insulator.

Referring to FIG. 15, the first halves of the contact terminals 21A to 21D are received respectively in four through holes 55 of a small diameter formed in the first half of the insulator 5 (in the drawings, only one contact terminal is shown). A groove 52 of a U-shaped cross-section is formed in an inner surface of each through hole 55 so as to extend axially from an end opening of the through hole 55 to a position near to the stepped portion 51. The ends of the retaining pieces 25 of each contact terminal 21 are fitted against an end of the U-shaped groove 52, as shown in FIG. 1.

With this construction, the upward movement of the contact terminal 21 is limited by the engagement of the bent portion 27 thereof with the stepped portion 51, and the downward movement thereof is limited by the engagement of the retaining pieces 25 with the end of the U-shaped groove 52.

For assembling the oxygen sensor, each of the lead wires 22 is passed through the respective holes 55 in the insulator 5. The lead wire 32 is pulled so that the contact terminal 21 connected to the lead wire 22 is brought into the insulator 5. The bent portion 27 is abutted against the stepped portion 51, thereby positioning the contact terminal. At this time, the retaining pieces 25 are inserted into the through hole 55 in a folded manner, and when these retaining pieces 25 become received in the groove 52, they are restored in an expanding direction by their resiliency to abut against the end of the groove 52.

Figure 16:
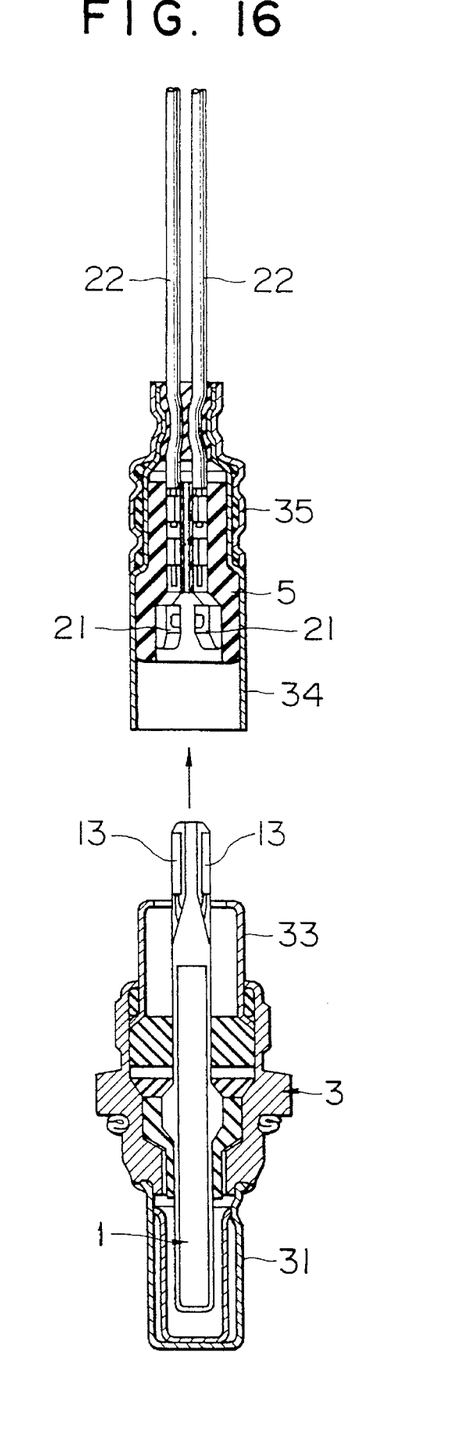
FIG. 16 is an exploded, perspective view of the oxygen sensor.

The insulator 5 having the four contact terminals 21A to 21D thus mounted thereon, the dust cover 34 and the filter cover 35 are assembled together into a sensor half by caulking the outer periphery of the filter cover 35 (FIG. 16). The sensor element 1 fixedly received in the housing 3 is inserted into the insulator 5, so that the contact terminals 21A to 21 D are brought respectively into electrical contact with the take-out electrodes 13A to 13D on the sensor element 1. The sensor cover 33 is connected to the dust cover 34 by caulking the latter.

In this embodiment, the contact terminal 21 can be readily and simply positioned so as not to be axially displaced by means of the stepped portion 51 and the U-shaped groove 52 both provided in the insulator 5. Therefore, even when the oscillating force is applied to the sensor, the contact terminals 21 will not be displaced out of position in any axial directions, and hence an imperfect electrical contact will not be encountered.

Moreover, since the contact terminals 21 can be smoothly inserted into the insulator 5, the assembling operation can be effected easily.

Figure 17:
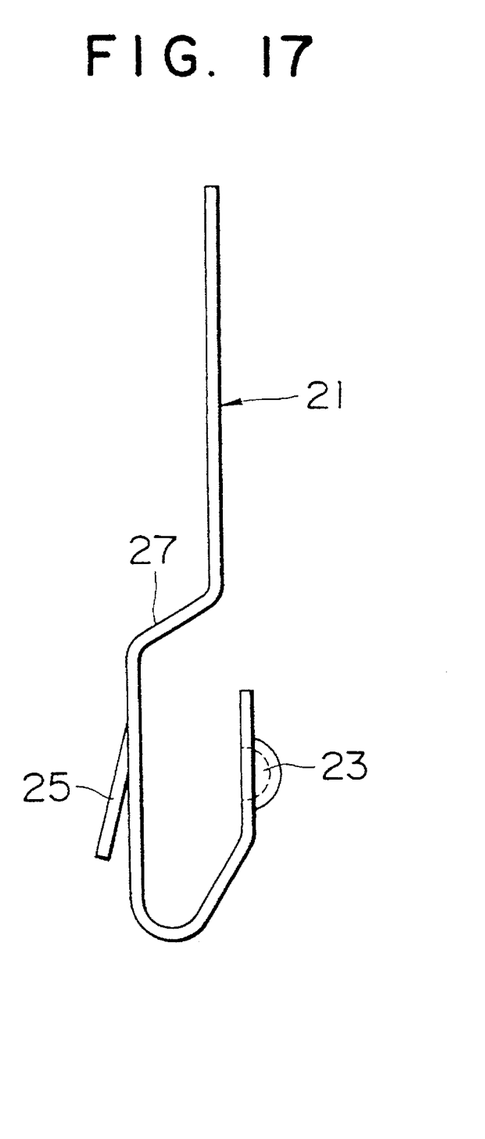
FIGS. 17 and 18 are side-elevational views of the respective modified contact terminals.
Figure 18:
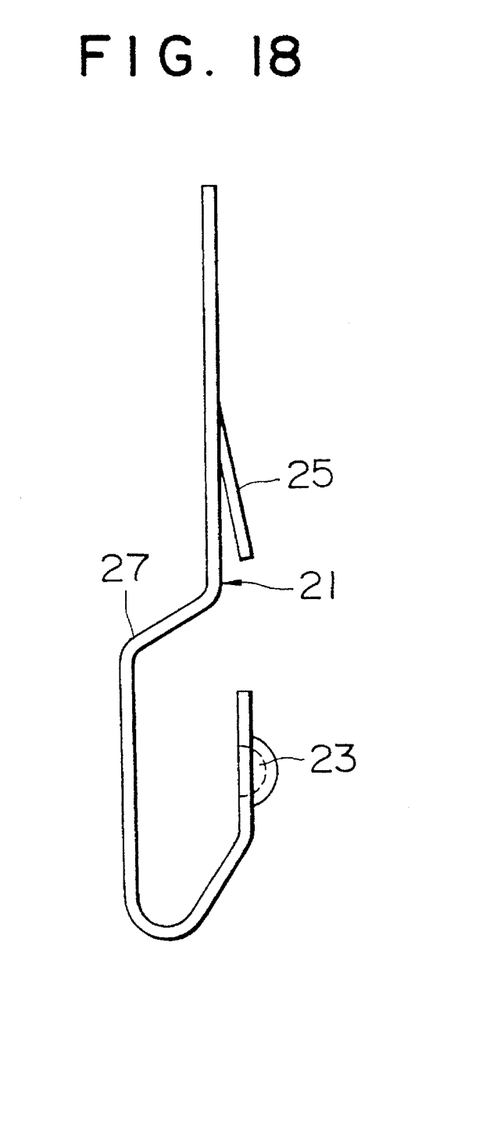

The present invention is not to be restricted to the above embodiments, and various modifications can be made. For example, depending on the shape and so on of the insulator 5, the retaining pieces 25 of the contact terminal 21 may be formed to extend obliquely from the rear surface of the proximal portion of the bent portion 27 as shown in FIG. 17, or may be formed to extend obliquely from the front surface of the central portion of the contact terminal as shown in FIG. 18.

What is claimed is:

1. A gas sensor comprising:
   a gas sensor plate for detecting a condition of a gas, said gas sensor plate having a first end portion that is exposed to the gas to be measured and a second end portion of a polygonal-sided pillar;
   a plurality of electrodes, each of said electrodes provided on a respective side surface of the polygonal-sided pillar;
   a tubular housing for receiving said gas sensor plate; and
   a plurality of contact terminals, each of said contact terminals electrically connected and corresponding to one of said electrodes of said gas sensor plate, said contact terminals applying pressing forces in directions toward said corresponding electrodes, the directions of said pressing forces of each of said contact terminals opposing the directions of the pressing forces of said contact terminals on the opposite side surface of said polygonal-sided pillar to hold said gas sensor plate within said tubular housing.

2. A gas sensor according to claim 1, wherein said polygonal-sided pillar has a substantially parallelogram cross-section, and wherein said electrodes are provided on the four side surfaces of the second end portion of the sensor element.

3. A gas sensor according to claim 1, wherein said polygonal-sided pillar is substantially rectangular and at least two corners thereof are chamfered, and wherein said electrodes are provided on at least three side surfaces of the second end portion of the sensor element.

4. A gas sensor according to claim 1, wherein said polygonal-sided pillar has a pair of side groups, each side group including adjacent two slanting side surfaces and a first flat side surface interconnecting said slanting side surfaces, and wherein said side groups are facing each other.

5. A gas sensor according to claim 4, wherein opposite ends of one side group are connected with opposite ends of the other side group through second flat side-surfaces so as to present an octagonal-sided pillar of the second end portion of said sensor element.

6. A gas sensor comprising:
   a gas sensor plate for detecting a condition of a gas, said gas sensor plate having a first end portion that is exposed to the gas to be measured and a second end portion of a polygonal-sided pillar, at least two corners of said polygonal-sided pillar being chamfered;
   a plurality of electrodes provided on at least said chamfered corners and one side surface of said polygonal-sided pillar;
   a tubular housing for receiving said gas sensor plate; and
   a plurality of contact terminals, each of said contact terminals electrically connected and corresponding to one of said electrodes of said gas sensor plate, said contact terminals applying pressing forces in directions toward said corresponding electrodes, the directions of said pressing forces of each of said contact terminals opposing the directions of the pressing forces of said contact terminals on the opposite side surface of said polygonal-sided pillar to hold said gas sensor plate within said tubular housing.

7. A gas sensor comprising:
   a gas sensor element having a first end portion that is exposed to a gas to be measured and a second end portion, said second end portion having a plurality of electrodes disposed on a peripheral surface thereof;
   a tubular housing for receiving therein said gas sensor element;
   a plurality of lead wires for transmitting signals from said gas sensor element;
   a plurality of terminals, each of said terminals having at one end portion thereof a proximal end portion electrically connected to one of said lead wires, and at another end portion thereof a contact portion electrically contacted with one of said electrodes, the proximal end portion and the contact portion of each of said terminals being integrated through a conductive portion, said conductive portion provided at the contact portion side thereof with a bent step portion and at the proximal end portion side thereof with an engaging portion, a free end of said engaging portion facing said bent step portion;
   a one-piece tubular insulator received in said tubular housing, said insulator provided with holes extending in an axial direction, said proximal end portion and said engaging portion of each of said terminals being received in a respective one of said holes, and a projection projecting from an inner surface of each of said holes so that when the proximal end portion of a respective one of said terminals is received in a corresponding one of said holes, said projection is located between said engaging portion and said bent step portion and said projection abuts said free end of said engaging portion and said bent step portion.

8. A gas sensor according to claim 7, wherein said contact portion of each of said terminals is U-shaped and in resilient contact with a corresponding one of said electrodes of said gas sensor element.

9. A gas sensor comprising:

a gas sensor element having a first end portion that is exposed to a gas to be measured and a second end portion, said second end portion having a plurality of electrodes disposed on a peripheral surface thereof;

a tubular housing for receiving therein said gas sensor element;

a plurality of lead wires for transmitting signals from said gas sensor element;

a plurality of terminals, each of said terminals having at one end portion thereof a proximal end portion electrically connected to one of said lead wires, and at another end portion thereof a contact portion electrically contacted with one of said electrodes, the proximal end portion and the contact portion of each of said terminals being integrated through a conductive portion, said conductive portion being provided at the contact portion side thereof with a bent step portion and at the proximal end portion side thereof with an engaging portion, a free end of said engaging portion facing said bent step portion;

a one-piece tubular insulator received in said tubular housing, said insulator provided with holes extending in an axial direction, said proximal end portion and said engaging portion of each of said terminals being received in a respective one of said holes, and each of said holes having an inner surface thereof with a projection and tapered portion facing said projection, so that when the proximal end portion of a respective one of said terminals is received in a corresponding one of said holes, said projection abuts said free end of said engaging portion and said bent step portion abuts said tapered portion.

10. A gas sensor according to claim 9, wherein said contact portion of each of said terminals is U-shaped and in resilient contact with a corresponding one of said electrodes of said gas sensor element.

11. A gas sensor comprising:

a gas sensor element having a first end portion that is exposed to a gas to be measured and a second end portion, said second end portion having a plurality of electrodes disposed on a peripheral surface thereof;

a tubular housing for receiving therein said gas sensor element;

a plurality of lead wires for transmitting signals from said gas sensor element;

a plurality of terminals, each of said terminals having at one end portion thereof a proximal end portion electrically connected to one of said lead wires, and at another end portion thereof a contact portion electrically contacted with one of said electrodes, the proximal end portion and the contact portion of said terminals being integrated through a conductive portion, said conductive portion having an engaging portion and being provided at the contact portion side thereof with a bent step portion, a free end of said engaging portion located between said bent step portion and said contact portion;

a one-piece tubular insulator received in said tubular housing, said insulator provided with holes extending in an axial direction, said proximal end portion and said engaging portion of each of said terminals being received in a respective one of said holes, each of said holes having at an inner surface thereof a tapered portion and a step portion facing said tapered portion so that when the proximal end portion of a respective one of said terminals is received in a corresponding one of said holes, said tapered portion abuts said bent step portion and said step portion abuts said free end of said engaging portion.

12. A gas sensor according to claim 11, wherein said contact portion of each of said terminals is U-shaped and in resilient contact with a corresponding one of said electrodes of said gas sensor element.

* * * * *